United States Patent
Günther et al.

(10) Patent No.: US 7,807,851 B2
(45) Date of Patent: Oct. 5, 2010

(54) METHOD FOR PRODUCING α-FLUOROMALONIC ACID DIALKYL ESTERS

(75) Inventors: Andreas Günther, Köln (DE); Holger Weintritt, Langenfeld (DE); Stefan Böhm, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 723 days.

(21) Appl. No.: 10/568,355

(22) PCT Filed: Aug. 13, 2004

(86) PCT No.: PCT/EP2004/009117
§ 371 (c)(1),
(2), (4) Date: Aug. 16, 2006

(87) PCT Pub. No.: WO2005/019154
PCT Pub. Date: Mar. 3, 2005

(65) Prior Publication Data
US 2007/0191628 A1    Aug. 16, 2007

(30) Foreign Application Priority Data
Aug. 18, 2003 (DE) ................... 103 37 885

(51) Int. Cl.
*C07C 69/34* (2006.01)

(52) U.S. Cl. ...................................... 560/192

(58) Field of Classification Search ............. 560/43, 560/51, 82, 172, 174, 192
See application file for complete search history.

(56) References Cited

U.S. PATENT DOCUMENTS

| 5,391,811 A | 2/1995 | Böhm et al. |
| 6,103,717 A | 8/2000 | Heinemann et al. |
| 2002/0006958 A1 | 1/2002 | Seitz et al. |

FOREIGN PATENT DOCUMENTS

| DE | 42 37 882 A1 | 5/1994 |
| DE | 100 41 618 A1 | 3/2002 |
| EP | 0 882 043 B1 | 9/2002 |
| EP | 0 970 057 B1 | 2/2006 |
| WO | WO 98/21189 A1 | 5/1998 |
| WO | WO 02/16304 A1 | 2/2002 |
| WO | WO0216304 * | 2/2002 |

OTHER PUBLICATIONS

Ishikawa, N., et al., "Preparation of 2-Fluoromalonic Esters and Related Compounds from Hexafluoropropene," *J. Fluorine Chemistry* 25:203-212, Elsevier Sequoia (1984).

International Search Report for International Application No. PCT/EP2004/009117, European Patent Office, Netherlands, mailed on Jan. 24, 2005.

* cited by examiner

*Primary Examiner*—Taylor Victor Oh
(74) *Attorney, Agent, or Firm*—Sterne, Kessler, Goldstein & Fox P.L.L.C.

(57) ABSTRACT

The invention relates to a new, advantageous method for the preparation of dialkyl α-fluoromalonates.

8 Claims, No Drawings

METHOD FOR PRODUCING α-FLUOROMALONIC ACID DIALKYL ESTERS

The invention relates to a new, advantageous method for the preparation of dialkyl α-fluoromalonates.

Dialkyl α-fluoromalonates are intermediates that are used, for example, in the preparation of 4,6-dichloro-5-fluoropyrimidine (cf. EP-A-0 970 057). 4,6-Dichloro-5-fluoropyrimidine is an important intermediate for the preparation of active compounds that are used as plant protection agents (cf. EP-A-0 882 043 and EP-A-0 937 050).

It is already known that α-fluoro-β-ketoesters of structure (I) can be obtained starting from α-chloro-β-ketoesters of structure (II) by reaction with an addition product of hydrogen fluoride and a trialkylamine at temperatures of 103° C. to 130° C. under pressure.

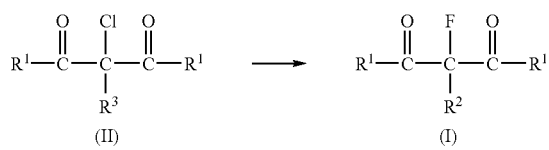

A fundamental disadvantage of this method is that work under pressure demands an increased outlay on equipment and special technical safety measures. For this reason this method is unsuitable for industrial use.

In another method (cf. DE-A-42 37 882) the preparation of α-fluoro-β-dicarbonyl compounds of structure (B) takes place starting from dicarbonyl compounds of structure (A) by reaction with an addition product of hydrogen fluoride and a trialkylamine at temperatures of 20° C. to 100° C.

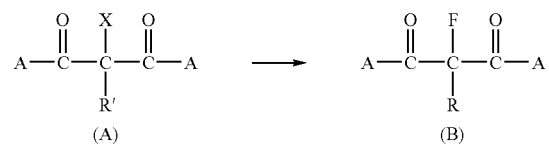

The disadvantage of this method for the preparation of dialkyl α-fluoromalonates is the long reaction time of 72 hours in spite of the use of large excesses of hydrogen fluoride and triethylamine.

The task of the present invention is to make available a method for the preparation of dialkyl α-fluoromalonates that allows preparation without the use of high pressure in good yields and shorter reaction times in spite of lower excess of hydrogen fluoride and triethylamine by which means the space-time yield is improved. In particular a method has to be found that is more environmentally friendly through the reduced consumption of starting materials.

It has now been found that dialkyl α-fluoromalonates of the general structure (I),

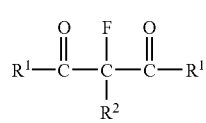

in which $R^1$ stands for alkoxy with 1 to 4 carbon atoms and
$R^2$ stands for hydrogen or fluorine are obtained when a dicarbonyl compound of the general structure (II),

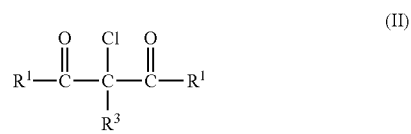

in which
$R^1$ has the meaning described above and
$R^3$ stands for hydrogen, fluorine or chlorine,
is reacted with an addition product of hydrogen fluoride and triethylamine at temperatures of 103° C. to 115° C.

In the compounds of structure (II) $R^1$ stands particularly for methoxy or ethoxy.

In the compounds of structure (II) $R^1$ stands most particularly for ethoxy.

In the compounds of structure (I) $R^2$ stands particularly for hydrogen.

The residue definitions cited above or described in the preferred ranges apply to both the starting compounds of structure (II) and correspondingly for the final product of structure (I).

It is considered highly surprising that with the method of the invention, which is operated under normal pressures and with only small excesses of hydrogen fluoride and triethylamine, an up to tenfold improvement in space-time yield can be achieved. It is especially surprising that dialkyl α-fluoromalonates are obtained in yields as good as with the methods described in the state of the art that are carried out at normal pressure and low temperature since the person skilled in the art expects partial decomposition and consequently lower yields at higher temperatures.

The method of the reaction exhibits a number of advantages. Thus dialkyl α-fluoromalonates are obtained in a fraction of the reaction time that is normal with known methods at normal pressure. According to the method of the invention the reaction time is 15 hours, whereas with known methods a reaction time of 72 hours is necessary (cf. DE-A 42 37 892). Of special significance is that a good space-time yield is obtained although the reaction can be carried out under normal pressure. A further advantage is that in spite of the relatively short reaction time only small excesses of hydrogen fluoride and triethylamine are necessary. The new method is thus suitable particularly for industrial use.

The dicarbonyl compounds of general structure (II) and all other starting compounds are accessible commercial products or can prepared from these by simple methods.

In carrying out the method of the invention addition products of hydrogen fluoride and triethylamine that are generally used contain 1 to 2 mols hydrogen fluoride per mol triethylamine, preferably 1.2 to 1.8 mols hydrogen fluoride, most preferably 1.4 to 1.5 mols.

In carrying out the method of the invention 1 to 4 mols triethylamine as addition product with hydrogen fluoride are generally used per mol of starting material of structure II, preferably 1.2 to 2.5 mols, more preferably 1.4 to 2 mols.

The addition products of hydrogen fluoride and triethylamine can be prepared in situ by the addition of triethylamine to liquid hydrogen fluoride. Alternatively the addition products of hydrogen fluoride and triethylamine can be prepared in situ by the addition of hydrogen fluoride to triethylamine.

The reaction temperatures can be varied over a small range when carrying out the method of the invention. In general temperatures of 103° C. to 115° C., preferably temperatures of 105° C. to 110° C. are used.

The method of the invention is carried out under normal pressure. Within the context of the present invention normal pressure is understood to be 800 to 1200 mbar.

In general the method of the invention is carried out as follows: the addition product of hydrogen fluoride and triethylamine is made ready in a reaction vessel. The dicarbonyl compounds of general structure (II) are added immediately or with warming. The reaction mixture is then heated to 105° C. to 110° C. and stirred. The reaction mixture is then cooled and treated with water. The organic phase is separated and where appropriate distilled. For better separation of the product from water, single or multiple use of an extraction solvent can be of advantage. For example, xylene, toluene or methylene chloride may be used.

Preferably stirring is continued at the reaction temperature until the optimum yield is achieved.

The method of the invention can be used, for example, in the preparation of diethyl α-fluoromalonate which can be used, for example, as intermediate in the preparation of 4,6-dichloro-5-fluoropyrimidine (cf. EP-A-970 057). 4,6-Dichloro-5-fluoropyrimidine can be used for the preparation of fluorine-substituted heterocycles that are, for example, biologically active or are of interest as intermediates for plant protection agents (cf. N. Ishikawa, J. Fluorine Chem. 1984, 25, 203, or EP-A 970 057).

The following example serves to illustrate the invention. However, the invention is not limited to the example.

PREPARATION EXAMPLES

Example 1

Diethyl α-Fluoromalonate

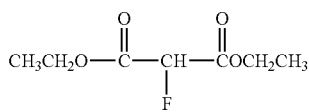

137 g (0.85 mol) triethylamine-trishydrofluoride are prepared. 86 g (0,85 mol) triethylamine are added at 80° C. Next 195 g (1 mol) diethyl α-chloromalonate are added over 2 hours at 80° C. Stirring is continued for 15 hours at reflux (105 to 110° C.) under normal pressure. To isolate the reaction product 200 g xylene are added to the reaction mixture at 60° C. followed by 215 g water and the phases are separated at 60° C. The aqueous phase is extracted with 100 g xylene.

The two organic phases are combined and distilled under reduced pressure. The first fraction is xylene. The second fraction (156 g) contains diethyl α-fluoromalonate of 96% content. That is 0.84 mol or 84% yield.

The invention claimed is:

1. A method for the preparation of compounds of the structure (I),

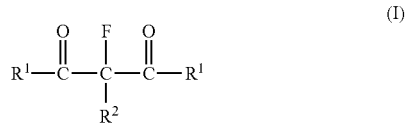

wherein
$R^1$ is alkoxy with 1 to 4 carbon atoms and
$R^2$ is hydrogen or fluorine,
comprising reacting a compound of structure (II),

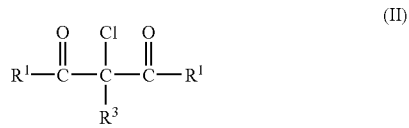

wherein
$R^1$ has the meaning described above and
$R^3$ is hydrogen, fluorine or chlorine,
with 1.4 to 2.0 mol equivalents of an addition product of hydrogen fluoride and triethylamine per mol of starting material of structure (II) at temperatures of 103° C. to 115° C. at 800 to 1200 mbar.

2. The method as described in claim 1, wherein $R^1$ is methoxy or ethoxy.

3. The method as described in claim 1, wherein $R^2$ and $R^3$ are hydrogen.

4. The method as described in claim 1, wherein the temperature is from 105° C. to 110° C.

5. The method as described in claim 1, wherein the addition product of hydrogen fluoride and triethylamine contains 1.2 to 1.8 mols hydrogen fluoride per mol triethylamine.

6. The method as described in claim 2, wherein $R^2$ and $R^3$ are hydrogen.

7. The method as described in claim 2, wherein the temperature is from 105° C. to 110° C.

8. The method as described in claim 2, wherein the addition product of hydrogen fluoride and triethylamine contains 1.2 to 1.8 mols hydrogen fluoride per mol triethylamine.

* * * * *